(12) United States Patent
Nag et al.

(10) Patent No.: US 11,760,743 B2
(45) Date of Patent: Sep. 19, 2023

(54) ACYLOXY SUBSTITUTED PHENYL DITHIANE DERIVATIVES

(71) Applicant: Renovel Innovations, Inc, Fremont, CA (US)

(72) Inventors: Bishwajit Nag, Union City, CA (US); Ananda Sen, Castro Valley, CA (US); Nitish Nag, Union City, CA (US); Arjun Sanyal, Castro Valley, CA (US); Srinivasan Narasimhan, Chennai (IN)

(*) Notice: Subject to any disclaimer, the term of this patent is extended or adjusted under 35 U.S.C. 154(b) by 0 days.

(21) Appl. No.: 17/499,684

(22) Filed: Oct. 12, 2021

(65) Prior Publication Data

US 2022/0235024 A1    Jul. 28, 2022

Related U.S. Application Data

(60) Provisional application No. 63/141,889, filed on Jan. 26, 2021.

(51) Int. Cl.
*C07D 339/08* (2006.01)
*C07D 409/12* (2006.01)
*C07D 211/60* (2006.01)
*C07D 401/12* (2006.01)

(52) U.S. Cl.
CPC .......... *C07D 339/08* (2013.01); *C07D 211/60* (2013.01); *C07D 401/12* (2013.01); *C07D 409/12* (2013.01)

(58) Field of Classification Search
CPC .................................................. C07D 339/08
See application file for complete search history.

(56) References Cited

U.S. PATENT DOCUMENTS 6,307,062 B1 * 10/2001 Caye .................... C07D 339/00
549/21

* cited by examiner

*Primary Examiner* — Golam M Shameem
(74) *Attorney, Agent, or Firm* — GSS Law group; Gregory Scott Smith (57) ABSTRACT

Para-acyl substituted diazacyclohexenes, medical formulations thereof and methods for making and using the same.

7 Claims, 4 Drawing Sheets

ACYLOXY SUBSTITUTED PHENYL DITHIANE DERIVATIVES

RELATIONSHIP TO OTHER APPLICATIONS

This patent claims the benefit of and priority to U.S. Provisional Application No. 63/141,889 filed Jan. 26, 2021, which is incorporated herein by reference.

FIELD OF THE INVENTION

The present invention relates to novel acyloxy substituted phenyl dithiane for the treatment of immunological diseases, inflammation, obesity, hyperlipidemia, hypertension, neurological diseases and diabetes.

BACKGROUND

Inflammation is part of the complex biological response of vascular tissues to harmful stimuli, such as pathogens, damaged cells, or irritants. The classical signs of acute inflammation are pain, heat, redness, swelling, and loss of function. Inflammation is a protective attempt by the organism to remove the injurious stimuli and to initiate the healing process. Inflammation is not a synonym for infection, even in cases where inflammation is caused by infection. Progressive destruction of the tissue would compromise the survival of the organism. However, chronic inflammation can also lead to a host of diseases, such as hayfever, periodontitis, atherosclerosis, rheumatoid arthritis, and even cancer (e.g., gallbladder carcinoma). Inflammation can be classified as either acute or chronic. Acute inflammation is the initial response of the body to harmful stimuli and is achieved by the increased movement of plasma and leukocytes (especially granulocytes) from the blood into the injured tissues. A cascade of biochemical events propagates and matures the inflammatory response, involving the local vascular system, the immune system, and various cells within the injured tissue. Prolonged inflammation, known as chronic inflammation, leads to a progressive shift in the type of cells present at the site of inflammation and is characterized by simultaneous destruction and healing of the tissue from the inflammatory process.

Drugs to treat acute and chronic inflammation are known as "Anti-inflammatory drugs". Anti-inflammatory drugs make up about half of analgesics, remedying pain by reducing inflammation as opposed to opioids, which affect the central nervous system.

Many steroids, to be specific glucocorticoids, reduce inflammation or swelling by binding to glucocorticoid receptors. These drugs are often referred to as corticosteroids. Non-steroidal anti-inflammatory drugs (NSAIDs), alleviate pain by counteracting the cyclooxygenase (COX) enzyme. On its own, COX enzyme synthesizes prostaglandins, creating inflammation. In whole, the NSAIDs prevent the prostaglandins from ever being synthesized, reducing or eliminating the pain.

Some common examples of NSAIDs are: aspirin, ibuprofen, and naproxen. The newer specific COX-inhibitors—although, it is presumed, sharing a similar mode of action—are not classified together with the traditional NSAIDs.

Long-term use of NSAIDs can cause gastric erosions, which can become stomach ulcers and in extreme cases can cause severe haemorrhage, resulting in death. The risk of death as a result of use of NSAIDs is 1 in 12,000 for adults aged 16-45. The risk increases almost 20-fold for those over 75. Other dangers of NSAIDs are exacerbating asthma and causing kidney damage. Apart from aspirin, prescription and over-the-counter NSAIDs also increase the risk of myocardial infarction and stroke.

A number of biological protein-based therapeutics especially monoclonal antibodies emerged as new class of treatment for inflammatory conditions specifically RA and IBD in recent years. These products are highly expensive and develop anti-idiotypic effects with chronic condition treatments. Therefore, need for new classes of anti-inflammatory molecules are in great demand. The present invention describes synthesis of new class of compounds originally isolated from natural product source and then structurally modified with minimum side effects.

SUMMARY

The present invention relates to novel acyloxy substituted phenyl dithiane of the formula (I)

and to their analogs, their tautomeric forms, their stereoisomers, their polymorphs, their pharmaceutically acceptable salts, and their pharmaceutically acceptable solvates, wherein $R_1$ is a hydrogen, or a straight chain or branched alkoxy derivative or a halogen, and X represents straight chain or branched alkane, alkene, alkyne and or aromatic or heterocyclic compound so as XOCl is always an aromatic or aliphatic acid chloride. The OOX bond can be present either in the ortho or para position to the group $R_1$ as represented by the Markush bond in formula (I).

The present invention also relates to a process for the preparation of the above said novel compounds, their analogs, their tautomeric forms, their stereoisomers, their polymorphs, their pharmaceutically acceptable salts, their pharmaceutically acceptable solvates, novel intermediates and pharmaceutical composites containing them. Tautomeric forms are isomeric forms which exists in a state of equilibrium capable of reacting according to either form. Stereoisomers include configurational isomers, such as cis- and trans double bonds, as well as optically active isomers having different spatial arrangements of their atoms. Polymorphs are molecules which can crystallize in two or more forms. Solvates are molecular or ionic complexes of molecules or ions of solvent with those of a solute. Analogs also include atoms of the same family of the Periodic Table, such as F, Cl, Br and I. Derivatives include compounds resulting from routine functionalizing of atoms, such as, derivatives found by protecting amino or carboxyl groups by carboxylation or esterification, respectively.

DESCRIPTION

Figure 1:
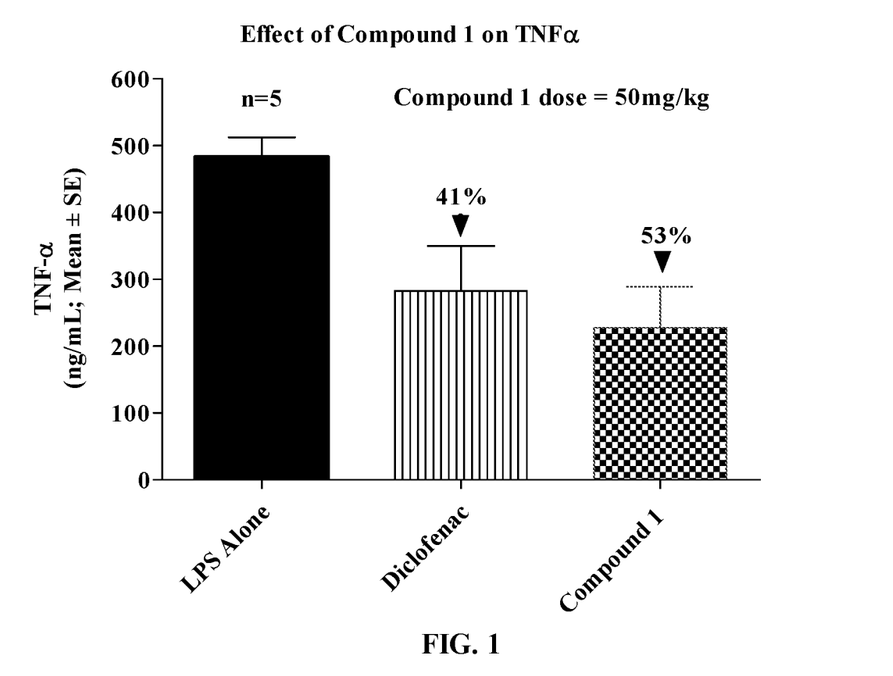
FIG. 1 shows that the group of mice administered with compound 1 showed a 53% decrease of TNF-α when compared to the control Lipopolysaccharide group.
Figure 2:
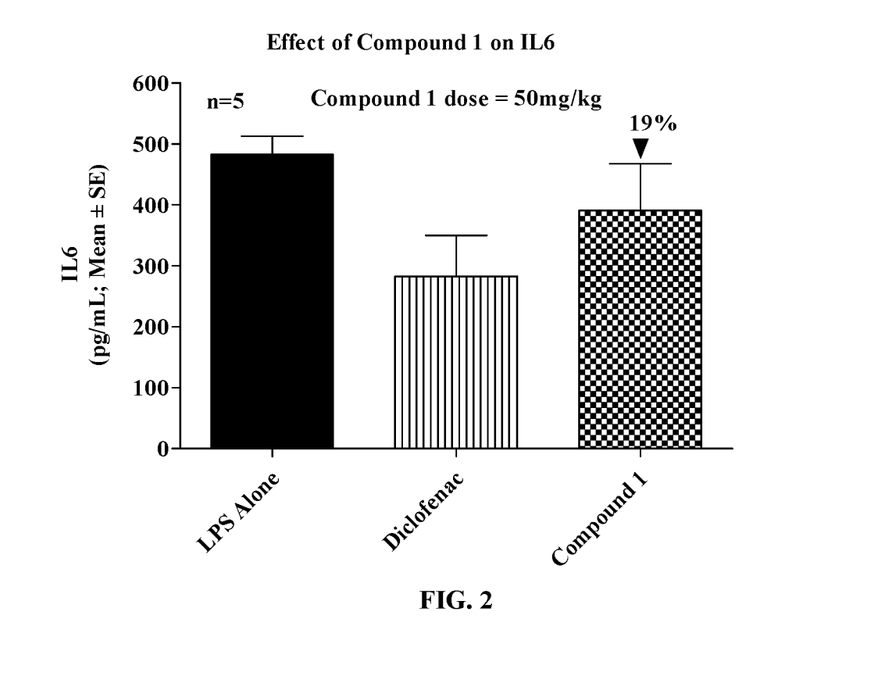
FIG. 2 shows that the group of mice administered with compound 1 showed a 19% decrease of IL-6 when compared to the control LPS group.
Figure 3A:
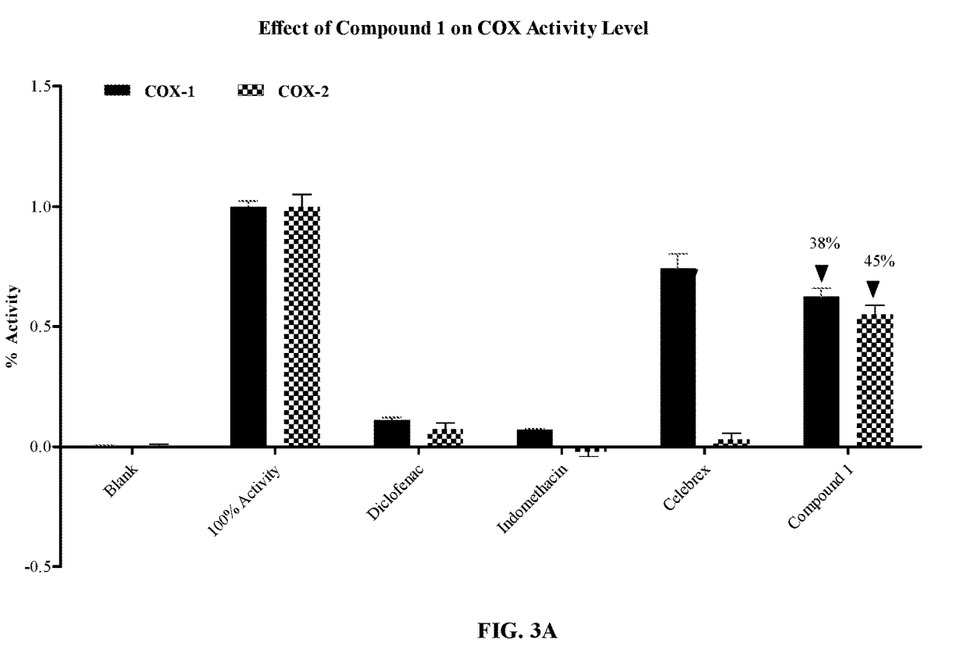
FIG. 3A shows that there is a greater reduction (45%) of COX-2 enzyme activity than COX-1 enzyme activity (38%).
Figure 3B:
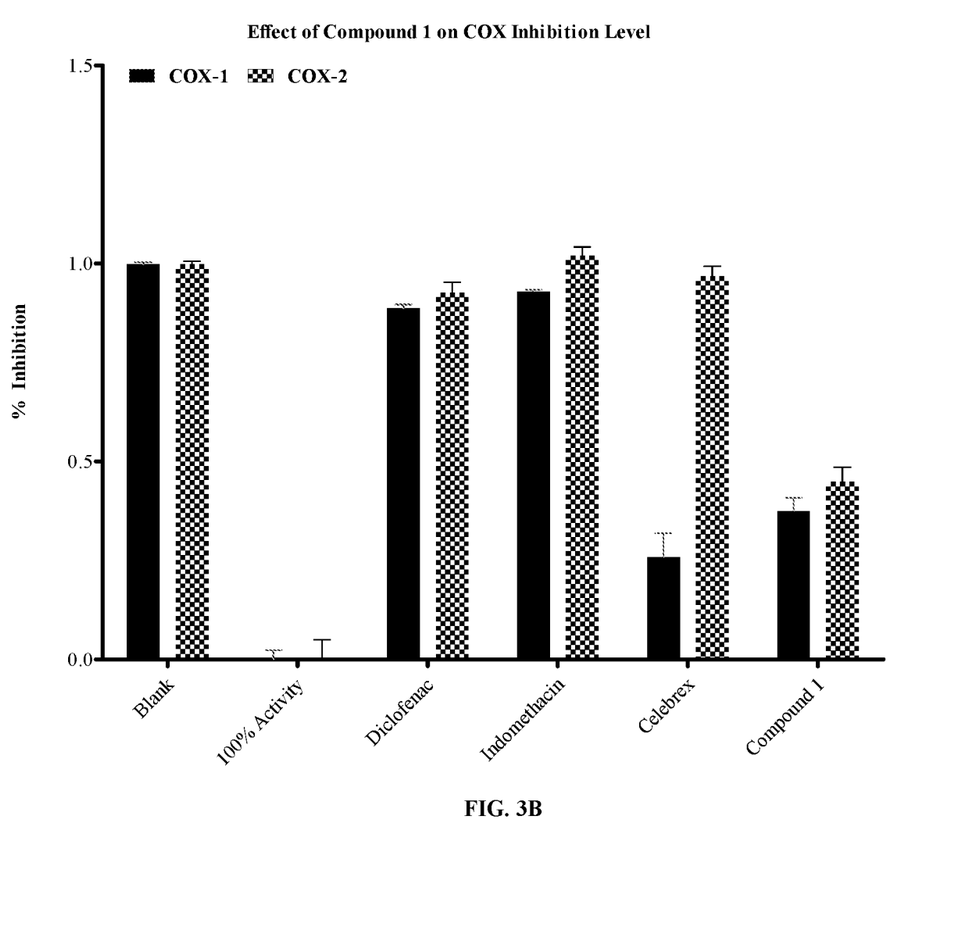
FIG. 3B shows the effect of compound 1 on COX-1 and COX-2 enzyme inhibition levels.
Figure 4:
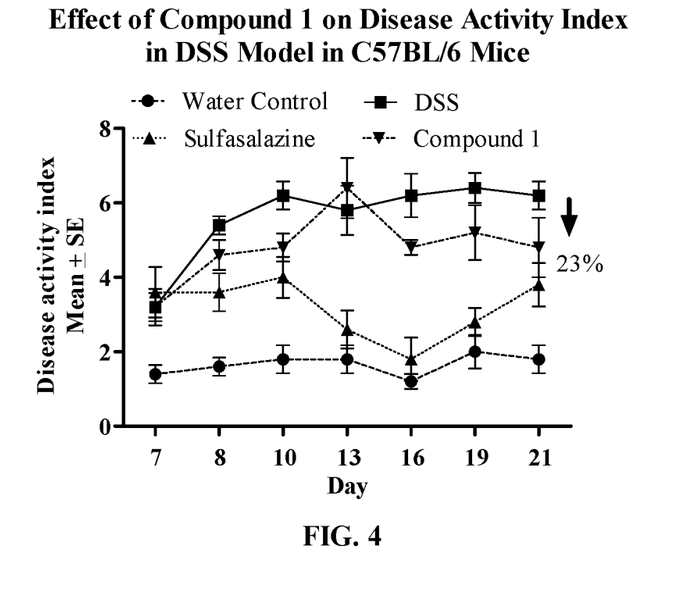
FIG. 4 shows that at the end of the study period of 21 days, the group of mice administered with compound 1 showed a significant (P<0.04) decrease by 23% in Disease Activity Index, compared with the vehicle DSS group.
Figure 5:
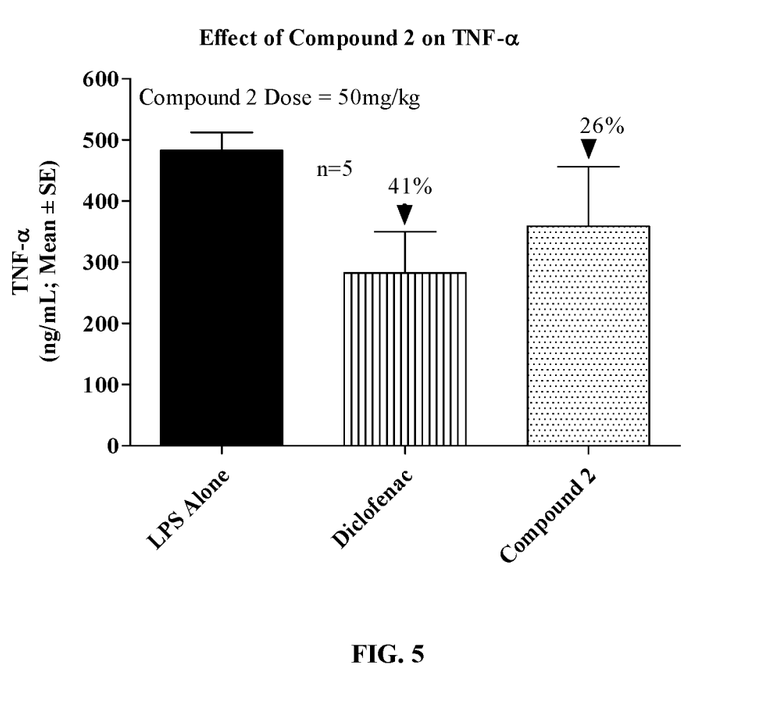
FIG. 5 shows that the group of mice administered with compound 2 showed a 26% decrease of TNF-α from the Control LPS group.

In an embodiment of the present invention, the group represented as $R_1$ is selected from hydrogen, straight chain or branched alkoxy derivatives and halogens such as fluorine, chlorine, bromine and iodine.

In an embodiment of the present invention, the group represented as X is selected from alkane, alkene, alkyne and or aromatic or heterocyclic compound so as XOCl is always an aromatic or aliphatic acid chloride.

Pharmaceutically acceptable salts forming part of this invention include base addition salts such as alkali metal salts like Li, Na, and K salts, alkaline earth metal salts like Ca and Mg salts, salts of organic bases such as lysine, arginine, guanidine, diethanolamine, chlorine and the like, ammonium or substituted ammonium salts. Salts may include acid addition salts which are sulphates, nitrates, phosphates, perchlorates, borates, hydrohalides, acetates, tartarates, maleates, citrates, succinates, palmoates, methanesulphonates, benzoates, ascorbates, glycerophosphates, ketoglutarates and the like. Pharmaceutically acceptable solvates may be hydrates or comprising other solvents of crystallization such as alcohols.

More preferably, the present innovation relates to novel acyloxy substituted phenyl dithiane of formula (I), (I)

their derivatives, their analogs, their tautomeric forms, their stereoisomers, their polymorphs, their pharmaceutically acceptable salts, their pharmaceutically acceptable solvates, novel intermediates and pharmaceutical composites containing them, wherein $R_1$ is hydrogen, straight chain or branched alkoxy derivatives or halogen and X represents straight chain or branched alkane, alkene, alkyne and or aromatic or heterocyclic compound so as XOCl is always an aromatic or aliphatic acid chloride. The OOX bond is present either in the ortho or para position to the group $R_1$ as represented by the Markush bond in formula (I).

The formula of the biologically active compounds synthesized in the present disclosure are listed below.

4-(1,3-dithian-2-yl)-2-methoxyphenyl cinnamate (compound 2)
4-(1,3-dithian-2-yl)phenyl cinnamate (compound 3)
(Z)-4-bromo-2-(1,3-dithian-2-yl)phenyl hex-3-enoate (compound 1)
2-(1,3-dithian-2-yl phenyl cinnamate
4-(1,3-dithian-2-yl)phenyl cinnamate
4-chloro-2-(1,3-dithian-2-yl phenyl cinnamate
2-chloro-4-(1,3-dithian-2-yl phenyl cinnamate
4-bromo-2-(1,3-dithian-2-yl phenyl cinnamate
2-bromo-4-(1,3-dithian-2-yl phenyl cinnamate
2-(1,3-dithian-2-yl)-4-methoxyphenyl cinnamate
4-(1,3-dithian-2-yl)-2-methoxyphenyl cinnamate
(Z)-2-(1,3-dithian-2-yl)phenyl 3-(4-bromophenyl)acrylate
(E)-4-(1,3-dithian-2-yl)phenyl 3-(4-bromophenyl)acrylate
(Z)-4-chloro-2-(1,3-dithian-2-yl)phenyl 3-(4-bromophenyl(acrylate
(E)-2-chloro-4-(1,3-dithian-2-yl)phenyl 3-(4-bromophenyl)acrylate
(Z)-4-bromo-2-(1,3-dithian-2-yl)phenyl 3-(4-bromophenyl)acrylate
(E)-2-bromo-4-(1,3-dithian-2-yl)phenyl 3-(4-bromophenyl)acrylate
(Z)-2-(1,3-dithian-2-yl)-4-methoxyphenyl 3-(4-bromophenyl)acrylate
(E)-4-(1,3-dithian-2-yl)-2-methoxyphenyl 3-(4-bromophenyl)acrylate
(Z)-2-(1,3-dithian-2-yl)phenyl 3-(pyridin-4-yl)acrylate
(E)-4-(1,3-dithian-2-yl)phenyl 3-(pyridin-4-yl)acrylate
(Z)-4-chloro-2-(1,3-dithian-2-yl)phenyl 3-(pyridin-4-yl)acrylate
(E)-2-chloro-2-(1,3-dithian-2-yl)phenyl 3-(pyridin-4-yl)acrylate
(Z)-4-bromo-2-(1,3-dithian-2-yl)phenyl 3-(pyridin-4-yl)acrylate
(E)-2-bromo-2-(1,3-dithian-2-yl)phenyl 3-(pyridin-4-yl)acrylate
(Z)-2-(1,3-dithian-2-yl)-4-methoxyphenyl 3-(pyridin-4-yl)acrylate
(E)-4-(1,3-dithian-2-yl)-4-methoxyphenyl 3-(pyridin-4-yl)acrylate
(Z)-2-(1,3-dithian-2-yl)phenyl 3-(2-chloropyridin-4-yl)acrylate
(E)-4-(1,3-dithian-2-yl)phenyl 3-(2-chloropyridin-4-yl)acrylate
(Z)-4-chloro-2-(1,3-dithian-2-yl)phenyl 3-(2-chloropyridin-4-yl)acrylate
(E)-2-chloro-2-(1,3-dithian-2-yl)phenyl 3-(2-chloropyridin-4-yl)acrylate
(Z)-4-bromo-2-(1,3-dithian-2-yl)phenyl 3-(2-chloropyridin-4-yl)acrylate
(Z)-2-(1,3-dithian-2-yl)-4-methoxyphenyl 3-(2-chloropyridin-4-yl)acrylate
(E)-4-(1,3-dithian-2-yl)-4-methoxyphenyl 3-(2-chloropyridin-4-yl)acrylate
(E)-2-(1,3-dithian-2-yl)phenyl hex-3-enoate
(Z)-4-(1,3-dithian-2-yl)phenyl hex-3-enoate
(E)-4-chloro-2-(1,3-dithian-2-yl)phenyl hex-3-enoate
(Z)-2-chloro-2-(1,3-dithian-2-yl)phenyl hex-3-enoate
(E)-4-bromo-2-(1,3-dithian-2-yl)phenylhex-3-enoate
(Z)-2-bromo-2-(1,3-dithian-2-yl)phenylhex-3-enoate
(E)-2-(1,3-dithian-2-yl)-4-methoxyphenyl hex-3-enoate
(Z)-4-(1,3-dithian-2-yl)-4-methoxyphenyl hex-3-enoate
2-(1,3-dithian-2-yl)phenyl 5-methylhexanoate
4-(1,3-dithian-2-yl)phenyl 5-methylhexanoate
4-chloro-2-(1,3-dithian-2-yl)phenyl 5-methylhexanoate
2-chloro-4-(1,3-dithian-2-yl)phenyl 5-methylhexanoate 4-bromo-2-(1,3-dithian-2-yl)phenyl 5-methylhexanoate

2-bromo-4-(1,3-dithian-2-yl)phenyl 5-methylhexanoate 2-(1,3-dithian-2-yl)-4-methoxyphenyl 5-methylhexanoate 4-(1,3-dithian-2-yl)-2-methoxyphenyl 5-methylhexanoate The list also consists of the IUPAC names of the compounds given in the table below—

| S. No | OOX | R₁ |
|---|---|---|
| 1. | cinnamate ester | H |
| 2. | cinnamate ester | Cl |
| 3. | cinnamate ester | Br |
| 4. | cinnamate ester | OCH₃ |
| 5. | 4-bromocinnamate ester | H |
| 6. | 4-bromocinnamate ester | Cl |
| 7. | 4-bromocinnamate ester | Br |
| 8. | 4-bromocinnamate ester | OCH₃ |
| 9. | pyridin-4-yl acrylate | H |
| 10. | pyridin-4-yl acrylate | Cl |
| 11. | pyridin-4-yl acrylate | Br |
| 12. | pyridin-4-yl acrylate | OCH₃ |
| 13. | 2-chloropyridin-4-yl acrylate | H |
| 14. | 2-chloropyridin-4-yl acrylate | Cl |

-continued

| S. No | OOX | R₁ |
|---|---|---|
| 15 | (acryloyl-2-chloropyridin-4-yl ester) | Br |
| 16 | (acryloyl-2-chloropyridin-4-yl ester) | OCH₃ |
| 17 | (pent-2-enoyl ester) | H |
| 18 | (pent-2-enoyl ester) | Cl |
| 19 | (pent-2-enoyl ester) | Br |
| 20 | (pent-2-enoyl ester) | OCH₃ |
| 21 | (4-methylpentanoyl ester) | H |
| 22 | (4-methylpentanoyl ester) | Cl |
| 23 | (4-methylpentanoyl ester) | Br |
| 24 | (4-methylpentanoyl ester) | OCH₃ |

Preferred salts for the compounds listed above are hydrochloride, hydrobromide, sodium, potassium or magnesium.

According to another feature of this present invention, there is provided a process for the preparation of the compound represented by the formula I, wherein all symbols are as defined as earlier, as shown in scheme-I

The reaction of a compound of general formula (1a) with a compound of general formula (2b) may be carried out using a polar protic solvent which may be selected from chloroform, ethanol, ethyl acetate and the like and in the presence of weak bases like DEA, TEA, Isopropylamine, pyridine, piperidine and the like, but more preferably with chloroform solvent and the base TEA. The reaction temperature may vary from 0 to 100° C., preferably in the range of 60-80° C., for example from 50-90° C., 65-75° C. or 60-70° C. The duration may range from 15 minutes to 5 hours. The product is obtained by suitable work up procedures including, for example, water and alkali washing and solvent concentration. The resulting compound has general formula (1c). The position of the bond OOX on compound of formula (1c) will depend on the position of the OH group in the compound of general formula (1a) taken as precursor. The bond may either be in the ortho or para position with respect to the aldehyde group in compounds of general formula (1a) and (1c).

The reaction of a compound of general formula (1c) with a compound of general formula (2a) may be carried out in the presence of a polar protic solvent such as chloroform or an alcohol which may be selected from methanol, ethanol, propanol and the like. More preferably the reaction is carried out in the presence of chloroform. The reaction temperature can vary between 5-100° C., preferably being in the range of 60-80° C. and the duration may range from 15 minutes to 5 hours and the final product may be precipitated directly or obtained by suitable work up procedures including, for example, water and alkali wash and solvent concentration. The final compound has general formula (3a) where the orientation of the bond OOX depends on the precursor (1a).

The invention is explained in detail in the examples given below which are provided by way of illustration only and therefore should not be construed to limit the scope of the invention.

Example 1

Synthesis of 4-(1,3-dithian-2-yl)phenyl cinnamate (Compound 3)

Step (i)

Synthesis of Cinnamoyl Chloride

Cinnamic acid (50.0 g) was taken in a clean and dry three neck round bottom flask and thionyl chloride (175 ml was added drop wise with constant stirring. The reaction mixture was refluxed at 70-80° C. for five hours. After reflux the excess thionyl chloride was distilled off. Hexane was added and distillation was performed again to remove any traces of thionyl chloride. The product was then transferred to an amberlite bottle and stored. (Yield 53.0 g).

Step (ii)

Synthesis of 3-phenyl-acrylic acid-4-formyl-phenyl ester 4-hydroxy benzaldehyde (14.69 g) was taken in a clean and dry two neck round bottom flask and chloroform (200 ml) was added with constant stirring. After the reaction mixture was cooled to 5-10° C., cinnamoyl chloride (20.0 g) was added drop wise. Stirring was continued for 15 minutes following which triethylamine (16.44 ml) was introduced. The reaction was allowed to proceed for 4 hours. It was then transferred into a beaker and washed twice with water (2×250 ml). The separated chloroform layer was shaken with 10% NaOH solution (2×250 ml), and then dried over anhydrous sodium sulphate. The chloroform was evaporated under reduced pressure and the precipitated solid was filtered and dried. 3-phenyl-acrylic acid-4-formyl-phenyl ester was produced with a yield of 15.70 g.

Step (iii)

Synthesis of 4-(1,3-dithian-2-yl)phenyl cinnamate (Compound 3)

3-phenyl-acrylic acid-4-formyl-phenyl ester (6.0 g) was taken in a clean and dry round bottom flask and chloroform (60 ml) was added. 1,3 propandithion (2.7 ml) and iodine (0.1 g) were introduced and the reaction mixture was stirred at room temperature for 3 hours following which it was quenched by transferring it into a beaker containing water (100 ml). The organic layer was separated and washed thrice with water, dried over sodium suphate and evaporated. The brown solid that was obtained was made into a slurry with by adding hexane and was filtered and dried to obtain the solid product. 4-(1,3-dithian-2-yl)phenyl cinnamate was produced with a yield of yield (7.0 g).

NMR-7.64 (1H,d), 7.14-7.30 (aromatic), 6.90-7.10 (aromatic), 6.40 (1H,d), 4.85 (1H,s), 2.45 (4H,t), 2.04 (2H,m).

Example 2

Synthesis of 4-(1,3-dithian-2-yl)-2-methoxyphenyl cinnamate (Compound 2)

Step (i)

Synthesis of Cinnamoyl Chloride

Cinnamic acid (50.0 g) was taken in a clean and dry three neck round bottom flask and thionyl chloride (175 ml) was added drop wise with constant stirring. The reaction mixture was refluxed at 70-80° C. for five hours. After reflux the excess thionyl chloride was distilled off. Hexane was added and distillation was performed again to remove any traces of thionyl chloride. The product was then transferred to an amberlite bottle and stored. (Yield 53.0 g).

Synthesis of Cinnamoyl Vanillin

Vanillin (22.8 g) was taken in a clean and dry round bottom flask and chloroform (200 ml) was added whilst stirring. The reaction mixture was cooled to 5-10° C. Cinnamoyl chloride (25.0 g) was added drop wise. Stirring was continued for another 15 minutes and TEA (20.55 ml) was added drop wise. The reaction was allowed to continue for 5 hours with constant stirring. The reaction mixture was then transferred to a 1 L beaker and washed twice with water (2×250 ml). The chloroform layer was separated and further washed with 10% NaOH solution (2×250 ml) and then dried with anhydrous sodium sulphate. The chloroform layer was then filtered and concentrated under vacuum. Hexane was then added to the concentrated chloroform layer and the solid formed was filtered and dried. (Yield 16.2 g).

Step (iii)

Synthesis of 4-(1,3-dithian-2-yl)-2-methoxyphenyl cinnamate (Compound 2)

Cinnamoyl vanillin (6.0) was taken in a clean and dry round bottom flask and chloroform (60 ml) was added. 1,3 propandithion (1.2 ml) and iodine (0.1 g) were introduced and the reaction mixture was stirred at room temperature for 3 hours following which it was quenched by transferring it into a beaker containing water (100 ml). The organic layer was separated and washed thrice with water, dried over sodium suphate and evaporated. The brown solid that was obtained was made into a slurry with by adding hexane and was filtered and dried to obtain the solid product. 4-(1,3-dithian-2yl)-2-methoxyphenyl cinnamate was produced with a yield of (7.0 g).

NMR—7.64 (1H,d), 7.14-7.30 (aromatic), 6.90-7.10 (aromatic), 6.40 (1H,d), 4.85 (1H,s), 3.75 (3H,s), 2.45 (4H,t), 2.04 (2H,m).

Example 3

Synthesis of (Z)-4-bromo-2-(1,3-dithian-2-yl)phenyl hex-3-enoate (compound 1)

Step (i)

Synthesis of (Z)-4-bromo-2-formyl phenyl hex-3-enoate 5-bromo salicyaldehyde (log) was taken in a clean and dry two neck round bottom flask and chloroform (100 ml) was added with constant stirring. The reaction mixture was cooled to 5-10° C. and (Z)-hex-3-enoylchloride (5.8 g) was added drop wise. Stirring was continued for 15 minutes and TEA (6.0 ml) was introduced. The reaction was allowed to proceed for 4 hours at room temperature with constant stirring following which it was quenched by transferring the reaction mixture into a beaker containing water. The separated chloroform layer was washed with 10% sodium bicarbonate solution (2×50 ml) followed by water (2×50 ml). The organic layer was then dried over anhydrous sodium sulfate and the solvent was evaporated to obtain the crude product. Yield (7.2 g).

Step (ii)

Synthesis of (Z)-4-bromo-2-(1,3-dithian-2-yl)phenyl hex-3-enoate

(Z)-4-bromo-2-formyl phenyl hex-3-enoate (1.0 g) was taken in a clean and dry round bottom flask and chloroform (25 ml) was added with constant stirring. 1,3 propandithiol (1.1 ml) was added drop wise and the reaction was allowed to proceed for 4 hours at room temperature. The solvent was then removed under reduced pressure to obtain the crude product. This solid obtained was washed with water and then with hexane, filtered and dried. Yield (0.56 g).

NMR-6.80-7.25 (Aromatic), 5.65 (2H,d), 4.86 (1H,s), 2.90 (1H,d), 2.45 (4H,t), 2.04 (4H,m), 1.10 (3H,t).

GENERAL DISCLOSURES

This specification incorporates by reference all documents referred to herein and all documents filed concurrently with this specification or filed previously in connection with this application, including but not limited to such documents which are open to public inspection with this specification. All numerical quantities mentioned herein include quantities that may be plus or minus 20% of the stated amount in every case, including where percentages are mentioned. As used in this specification, the singular forms "a, an", and "the" include plural reference unless the context clearly dictates otherwise. Thus, for example, a reference to "a part" includes a plurality of such parts, and so forth. The term "comprises" and grammatical equivalents thereof are used in this specification to mean that, in addition to the features specifically identified, other features are optionally present. For example, a composition "comprising" (or "which comprises") ingredients A, B and C can contain only ingredients A, B and C, or can contain not only ingredients A, B and C but also one or more other ingredients. The term "consisting essentially of" and grammatical equivalents thereof is used herein to mean that, in addition to the features specifically identified, other features may be present which do not materially alter the claimed invention. The term "at least" followed by a number is used herein to denote the start of a range beginning with that number (which may be a range having an upper limit or no upper limit, depending on the variable being defined). For example, "at least 1" means 1 or more than 1, and "at least 80%" means 80% or more than 80%. The term "at most" followed by a number is used herein to denote the end of a range ending with that number (which may be a range having 1 or 0 as its lower limit, or a range having no lower limit, depending upon the variable being defined). For example, "at most 4" means 4 or less than 4, and "at most 40%" means 40% or less than 40%. Where reference is made in this specification to a method comprising two or more defined steps, the defined steps can be carried out in any order or simultaneously (except where the context excludes that possibility), and the method can optionally include one or more other steps which are carried out before any of the defined steps, between two of the defined steps, or after all the defined steps (except where the context excludes that possibility). When, in this specification, a range is given as "(a first number) to (a second number)" or "(a first number)-(a second number)", this means a range whose lower limit is the first number and whose upper limit is the second number. For example, "from 40 to 70 microns" or "40-70 microns" means a range whose lower limit is 40 microns, and whose upper limit is 70 microns.

The invention claimed is:
1. A compound of formula (I)

wherein X is selected from the group consisting of alkanes, alkenes, alkynes, and aromatic or heterocyclic derivatives of an acid chloride, wherein $R_1$ is selected from the group consisting of a hydrogen, a halogen, a straight chain alkoxy group, and a branched alkoxy group, and pharmaceutically acceptable salts thereof, and further wherein the compound comprises a structure selected from the group consisting of:

| OOX | $R_1$ | IUPAC-OOX para to $R_1$ | IUPAC-OOX ortho to $R_1$ |
|---|---|---|---|
| cinnamate phenyl | H | 2-(1,3-dithian-2-yl)phenyl cinnamate | 4-(1,3-dithian-2-yl)phenyl cinnamate |
| cinnamate phenyl | Cl | 4-chloro-2-(1,3-dithian-2-yl)phenyl cinnamate | 2-chloro-4-(1,3-dithian-2-yl)phenyl cinnamate |
| cinnamate phenyl | Br | 4-bromo-2-(1,3-dithian-2-yl)phenyl cinnamate | 2-bromo-4-(1,3-dithian-2-yl)phenyl cinnamate |
| cinnamate phenyl | OCH$_3$ | 2-(1,3-dithian-2-yl)-4-methoxyphenyl cinnamate | 4-(1,3-dithian-2-yl)-2-methoxyphenyl cinnamate |
| 4-bromophenyl acrylate | H | (Z)-2-(1,3-dithian-2-yl)phenyl 3-(4-bromophenyl)-acrylate | (E)-4-(1,3-dithian-2-yl)phenyl 3-(4-bromophenyl)-acrylate |
| 4-bromophenyl acrylate | Cl | (Z)-4-chloro-2-(1,3-dithian-2-yl)phenyl 3-(4-bromophenyl)-acrylate | (E)-2-chloro-4-(1,3-dithian-2-yl)phenyl 3-(4-bromophenyl)-acrylate |
| 4-bromophenyl acrylate | Br | (Z)-4-bromo-2-(1,3-dithian-2-yl)phenyl 3-(4-bromophenyl)-acrylate | (E)-2-bromo-4-(1,3-dithian-2-yl)phenyl 3-(4-bromophenyl)-acrylate |
| 4-bromophenyl acrylate | OCH$_3$ | (Z)-2-(1,3-dithian-2-yl)-4-methoxyphenyl 3-(4-bromophenyl)-acrylate | (E)-4-(1,3-dithian-2-yl)-2-methoxyphenyl 3-(4-bromophenyl)-acrylate |
| pyridin-4-yl acrylate | H | (Z)-2-(1,3-dithian-2-yl)phenyl 3-(pyridin-4-yl)acrylate | (E)-4-(1,3-dithian-2-yl)phenyl 3-(pyridin-4-yl)acrylate |
| pyridin-4-yl acrylate | Cl | (Z)-4-chloro-2-(1,3-dithian-2-yl)phenyl 3-(pyridin-4-yl)acrylate | (E)-2-chloro-2-(1,3-dithian-2-yl)phenyl 3-(pyridin-4-yl)acrylate |
| pyridin-4-yl acrylate | Br | (Z)-4-bromo-2-(1,3-dithian-2-yl)phenyl 3-(pyridin-4-yl)acrylate | (E)-2-bromo-2-(1,3-dithian-2-yl)phenyl 3-(pyridin-4-yl)acrylate |
| pyridin-4-yl acrylate | OCH$_3$ | (Z)-2-(1,3-dithian-2-yl)-4-methoxyphenyl 3-(pyridin-4-yl)acrylate | (E)-4-(1,3-dithian-2-yl)-4-methoxyphenyl 3-(pyridin-4-yl)acrylate |
| 2-chloropyridin-4-yl acrylate | H | (Z)-2-(1,3-dithian-2-yl)phenyl 3-(2-chloropyridin-4-yl)acrylate | (E)-4-(1,3-dithian-2-yl)phenyl 3-(2-chloropyridin-4-yl)acrylate |
| 2-chloropyridin-4-yl acrylate | Cl | (Z)-4-chloro-2-(1,3-dithian-2-yl)phenyl 3-(2-chloropyridin-4-yl)acrylate | (E)-2-chloro-2-(1,3-dithian-2-yl)phenyl 3-(2-chloropyridin-4-yl)acrylate |
| 2-chloropyridin-4-yl acrylate | Br | (Z)-4-bromo-2-(1,3-dithian-2-yl)phenyl 3-(2-chloropyridin-4-yl)acrylate | (E)-2-bromo-2-(1,3-dithian-2-yl)phenyl 3-(2-chloropyridin-4-yl)acrylate |

| OOX | R₁ | IUPAC-OOX para to R₁ | IUPAC-OOX ortho to R₁ |
|---|---|---|---|
| (structure: cinnamate with 2-chloropyridin-4-yl) | OCH₃ | (Z)-2-(1,3-dithian-2-yl)-4-methoxyphenyl 3-(2-chloropyridin-4-yl)acrylate | (E)-4-(1,3-dithian-2-yl)-4-methoxyphenyl 3-(2-chloropyridin-4-yl)acrylate |
| (structure: hex-3-enoate) | H | (E)-2-(1,3-dithian-2-yl)phenyl hex-3-enoate | (Z)-4-(1,3-dithian-2-yl)phenyl hex-3-enoate |
| (structure: hex-3-enoate) | Cl | (E)-4-chloro-2-(1,3-dithian-2-yl)phenyl hex-3-enoate | (Z)-2-chloro-2-(1,3-dithian-2-yl)phenyl hex-3-enoate |
| (structure: hex-3-enoate) | Br | (E)-4-bromo-2-(1,3-dithian-2-yl)phenyl hex-3-enoate | (Z)-2-bromo-2-(1,3-dithian-2-yl)phenyl hex-3-enoate |
| (structure: hex-3-enoate) | OCH₃ | (E)-2-(1,3-dithian-2-yl)-4-methoxyphenyl hex-3-enoate | (Z)-4-(1,3-dithian-2-yl)-4-methoxyphenyl hex-3-enoate |
| (structure: 5-methylhexanoate) | H | 2-(1,3-dithian-2-yl)phenyl 5-methylhexanoate | 4-(1,3-dithian-2-yl)phenyl 5-methylhexanoate |
| (structure: 5-methylhexanoate) | Cl | 4-chloro-2-(1,3-dithian-2-yl)phenyl 5-methylhexanoate | 2-chloro-4-(1,3-dithian-2-yl)phenyl 5-methylhexanoate |
| (structure: 5-methylhexanoate) and | Br | 4-bromo-2-(1,3-dithian-2-yl)phenyl 5-methylhexanoate | 2-bromo-4-(1,3-dithian-2-yl)phenyl 5-methylhexanoate |
| (structure: 5-methylhexanoate) | OCH₃ | 2-(1,3-dithian-2-yl)-4-methoxyphenyl 5-methylhexanoate | 4-(1,3-dithian-2-yl)-2-methoxyphenyl 5-methylhexanoate. |

2. The compound of claim 1, wherein OOX may be present either at the ortho position or the para position with respect to the R₁ group.

3. The compound of claim 1, wherein said pharmaceutically acceptable salts consist of base addition salts.

4. The compound of claim 1 wherein the salt is selected from an alkali metal salt of Li, Na, or K, and an alkaline earth metal salt of Ca or Mg.

5. The compound of claim 1 wherein the salt is selected a salt of an organic base, and an ammonium or a substituted ammonium salt.

6. The compound of claim 1 wherein the salt is selected from a sulphate, a nitrate, a phosphate, a perchlorate, a borate, a hydro halide, an acetate, a tartarate, a maleate, a citrate, a succinate, a palmoate, a methanesulphonate, a benzoate, an ascorbate, a glycerophosphate, and a ketoglutarate salt.

7. The compound of claim 1 selected from the group consisting of:
4-(1,3-dithian-2-yl)-2-methoxyphenyl cinnamate (compound 2)
4-(1,3-dithian-2-yl)phenyl cinnamate (compound 3)
(Z)-4-bromo-2-(1,3-dithian-2-yl)phenyl hex-3-enoate (compound 1)
2-(1,3-dithian-2-yl)phenyl cinnamate
4-(1,3-dithian-2-yl)phenyl cinnamate
4-chloro-2-(1,3-dithian-2-yl)phenyl cinnamate
2-chloro-4-(1,3-dithian-2-yl)phenyl cinnamate
4-bromo-2-(1,3-dithian-2-yl)phenyl cinnamate
2-bromo-4-(1,3-dithian-2-yl)phenyl cinnamate
2-(1,3-dithian-2-yl)-4-methoxyphenyl cinnamate
4-(1,3-dithian-2-yl)-2-methoxyphenyl cinnamate
(Z)-2-(1,3-dithian-2-yl)phenyl 3-(4-bromophenyl)acrylate
(E)-4-(1,3-dithian-2-yl)phenyl 3-(4-bromophenyl)acrylate
(Z)-4-chloro-2-(1,3-dithian-2-yl)phenyl 3-(4-bromophenyl)acrylate
(E)-2-chloro-4-(1,3-dithian-2-yl)phenyl 3-(4-bromophenyl)acrylate
(Z)-4-bromo-2-(1,3-dithian-2-yl)phenyl 3-(4-bromophenyl)acrylate
(E)-2-bromo-4-(1,3-dithian-2-yl)phenyl 3-(4-bromophenyl)acrylate
(Z)-2-(1,3-dithian-2-yl)-4-methoxyphenyl 3-(4-bromophenyl)acrylate
(E)-4-(1,3-dithian-2-yl)-2-methoxyphenyl 3-(4-bromophenyl)acrylate
(Z)-2-(1,3-dithian-2-yl)phenyl 3-(pyridin-4-yl)acrylate
(E)-4-(1,3-dithian-2-yl)phenyl 3-(pyridin-4-yl)acrylate
(Z)-4-chloro-2-(1,3-dithian-2-yl)phenyl 3-(pyridin-4-yl)acrylate
(E)-2-chloro-4-(1,3-dithian-2-yl)phenyl 3-(pyridin-4-yl)acrylate
(Z)-4-bromo-2-(1,3-dithian-2-yl)phenyl 3-(pyridin-4-yl)acrylate
(E)-2-bromo-2-(1,3-dithian-2-yl)phenyl 3-(pyridin-4-yl)acrylate
(Z)-2-(1,3-dithian-2-yl)-4-methoxyphenyl 3-(pyridin-4-yl)acrylate
(E)-4-(1,3-dithian-2-yl)-4-methoxyphenyl 3-(pyridin-4-yl)acrylate
(Z)-2-(1,3-dithian-2-yl)phenyl 3-(2-chloropyridin-4-yl)acrylate
(E)-4-(1,3-dithian-2-yl)phenyl 3-(2-chloropyridin-4-yl)acrylate
(Z)-4-chloro-2-(1,3-dithian-2-yl)phenyl 3-(2-chloropyridin-4-yl)acrylate
(E)-2-chloro-2-(1,3-dithian-2-yl)phenyl 3-(2-chloropyridin-4-yl)acrylate
(Z)-4-bromo-2-(1,3-dithian-2-yl)phenyl 3-(2-chloropyridin-4-yl)acrylate
(E)-2-bromo-2-(1,3-dithian-2-yl)phenyl 3-(2-chloropyridin-4-yl)acrylate
(Z)-2-(1,3-dithian-2-yl)-4-methoxyphenyl 3-(2-chloropyridin-4-yl)acrylate
(E)-4-(1,3-dithian-2-yl)-4-methoxyphenyl 3-(2-chloropyridin-4-yl)acrylate (E)-2-(1,3-dithian-2-yl)phenyl hex-3-enoate
(Z)-4-(1,3-dithian-2-yl)phenyl hex-3-enoate
(E)-4-chloro-2-(1,3-dithian-2-yl)phenyl hex-3-enoate
(Z)-2-chloro-2-(1,3-dithian-2-yl)phenyl hex-3-enoate
(E)-4-bromo-2-(1,3-dithian-2-yl)phenyl hex-3-enoate
(Z)-2-bromo-2-(1,3-dithian-2-yl)phenyl hex-3-enoate
(E)-2-(1,3-dithian-2-yl)-4-methoxyphenyl hex-3-enoate
(Z)-4-(1,3-dithian-2-yl)-4-methoxyphenyl hex-3-enoate
2-(1,3-dithian-2-yl)phenyl 5-methylhexanoate
4-(1,3-dithian-2-yl)phenyl 5-methylhexanoate
4-chloro-2-(1,3-dithian-2-yl)phenyl 5-methylhexanoate
2-chloro-4-(1,3-dithian-2-yl)phenyl 5-methylhexanoate
4-bromo-2-(1,3-dithian-2-yl)phenyl 5-methylhexanoate
2-bromo-4-(1,3-dithian-2-yl)phenyl 5-methylhexanoate
2-(1,3-dithian-2-yl)-4-methoxyphenyl 5-methylhexanoate, and
4-(1,3-dithian-2-yl)-2-methoxyphenyl 5-methylhexanoate
and hydrochloride, hydrobromide, sodium, potassium or magnesium salts thereof.

* * * * *